United States Patent [19]

Yamada et al.

[11] Patent Number: 4,605,625

[45] Date of Patent: Aug. 12, 1986

[54] PROCESS FOR PRODUCING S-ADENOSYL-L-HOMOCYSTEINE

[75] Inventors: Hideaki Yamada; Sakayu Shimizu, both of Kyoto; Shozo Shiozaki, Kamakura, all of Japan

[73] Assignee: Nippon Zeon Co., Ltd., Tokyo, Japan

[21] Appl. No.: 706,393

[22] Filed: Feb. 27, 1985

[30] Foreign Application Priority Data

Feb. 27, 1984 [JP] Japan .................................. 59-35566

[51] Int. Cl.$^4$ ........................ C07P 41/00; C12P 19/26; C12P 19/28; C12P 19/40
[52] U.S. Cl. ..................................... 435/280; 435/84; 435/85; 435/88; 435/113; 435/118; 435/119; 435/193; 435/829; 435/874; 435/877; 435/929; 435/940
[58] Field of Search ............... 435/280, 113, 84, 118, 435/119, 193, 874, 877, 829, 940, 929, 911, 85, 88

[56] References Cited

U.S. PATENT DOCUMENTS 4,080,259 3/1978 Boesten et al. ...................... 435/280

OTHER PUBLICATIONS

Chemical Abstract I: 98: 194538y (1983) *Prep. Biochem.*, 12(5) 395–415.

*Primary Examiner*—Sidney Marantz
*Assistant Examiner*—L. Krawczewicz
*Attorney, Agent, or Firm*—Sherman and Shalloway

[57] ABSTRACT

S-adenosyl-L-homocysteine is produced by contacting adenosine with D-homocysteine in an aqueous medium in the presence of cells or treated cells of a microorganism of the genus Pseudomonas having the ability to racemize D-homocysteine to DL-homocysteine and in the presence of S-adenosyl-L-homocysteine hydrolase, to synthesize S-adenosyl-L-homocysteine, and thereafter collecting it.

15 Claims, No Drawings

PROCESS FOR PRODUCING S-ADENOSYL-L-HOMOCYSTEINE

This invention relates to a process for enzymatically synthesizing S-adenosyl-L-homocysteine efficiently from adenosine and homocysteine using cells or treated cells of a microorganism as an enzyme source, and collecting the synthesized product.

S-Adenosyl-L-homocysteine (to be abbreviated SAH hereinafter) is an important biologically active substance formed by a methyl group donating reaction in vivo in which S-adenosyl methionine (to be abbreviated SAM) participates. Recently, SAH was found to be efficacious as a sedative and a sleep inducing agent, and its production in quantities has been desired.

Conventional methods for producing SAH include, for example, extraction from yeasts of the genus Saccharomyces or Candida [for example, Arch. Biochem. Biophys., 69, 575 (1962)], enzymatic demethylation of SAM [for example, J. Biol. Chem., 240, 2112 (1965)], and chemical demethylation of SAM (for example, U.S. Pat. No. 3,642,772). These methods, however, are very costly and not industrially feasible.

A method has also been known for the enzymatic synthesis of SAH from adenosine and homocysteine in the presence of S-adenosyl-L-homocysteine hydrolase (EC 3.3.1.1; to be abbreviated SAHase). It is known however that only L-homocysteine can be used in this method, and D-homocysteine does not react by this method [for example, J. Bacteriology, 112, 569 (1972)].

In view of the foregoing background, the present inventors have extensively studied the enzymatic synthesis of SAH, and now found that SAH can be efficiently synthesized from D-homocysteine when a specific microorganism is used in the copresence of SAHase.

Thus, according to this invention, there is provided a process for producing S-adenosyl-L-homocysteine which comprises contacting adenosine with D-homocysteine in an aqueous medium in the presence of cells or treated cells of a microorganism of the genus Pseudomonas having the ability to racemize D-homocysteine to DL-homocysteine and in the presence S-adenosyl-L-homocysteine hydrolase to synthesize S-adenosyl-L-homocysteine, and thereafter collecting it.

The microorganism having the ability to racemize D-homocysteine to DL-homocysteine may include those microorganisms of the genus Pseudomonas which in the form of cells or treated cells have the ability to racemize D-homocysteine to DL-homocysteine but have no ability to racemize SAH to S-adenosyl-DL-homocysteine. Specific examples include *Pseudomonas putide* (IFO 12996 and IFO 3738), *Pseudomonas aeruginosa* (IFO 3445), and *Pseudomonas maltophilia (IFO 12020)*. Natural or artificial mutants of these microorganism strains can equally be used in this invention if they have the aforesaid properties.

The method of this invention to synthesize SAH utilizes the action of an enzyme capable of racemizing D-homocysteine to DL-homocysteine (to be abbreviated racemase) which exists within the cells or treated cells of the microorganism. The racemase can be prepared by cultivating the microorganism by an ordinary method. For this purpose, an ordinary culture medium may be used which contains carbon sources, nitrogen sources, inorganic salts and minor amounts of organic nutrient sources. It is selected properly depending upon the kind of the microorganism. The cultivation is usually carried out in a liquid medium, but solid surface culture may also be employed. The cultivation conditions may be properly selected according to the kind of the microorganism, and temperatures of 15° to 80° C. and a pH in the range of 4 to 12 may be used. Generally, the cultivation is carried out at a temperature of 20° to 45° C. and a pH of 4 to 9 for 10 to 96 hours. The growth of the microorganism may be promoted by aerating and agitating the culture medium during the cultivation.

SAHase used in this invention may be of any origin if it has the enzymatic activity of synthesizing SAH from adenosine and L-homocysteine. For example, those hydrolases which can be obtained from animal, plant or microorganism origins can be properly selected. For industrial practice, it is very advantageous to use SHAase in the form of cells or treated cells containing SAHase.

Specific examples of microorganisms containing SAHase are those of the genera Alcaligenes, Saccharomyces, Gibberella, Micropolyspora, Shizophyllum, etc. More specfically, any of the microorganisms described in U.S. Ser. No. 578,769 or French Patent Application No. 8401990 previously filed by the present inventors may be used. Such microorganisms may be cultivated in ordinary media under ordinary cultivating conditions.

The reaction of synthesizing SAH in accordance with this invention is carried out in the copresence of SAHase and the cells or treated cells of the microorganism cultivated as above and containing racemase. For example, simple mixing of the culture broth containing the cells of the microorganism having racemase with the culture broth containing the cells of the microorganism having SAHase induces the reaction of synthesizing SAH. However, when the components of the culture broths are detrimental or, it is desired to use large amounts of the cells, it is preferred to separate the cells from the culture broth and use them in the form of resting cells.

For convenience in storage or handling, dry cells such as air-dried cells, lyophilized cells and acetone-treated cells may be used instead of the living cells. They can also be used as treated cells such as crushed cells or cell-free extracts. These cells or treated cells may be used in the immobilized state.

The reaction of synthesizing SAH in this invention is carried out by contacting adenosine with D-homocysteine in the presence of the cells or treated cells containing racemase and SAHase in an aqueous medium. D-homocysteine used in the reaction needs not to be entirely pure, and a mixture of it with the L-form, for example DL-form, can also be used. The use of homocysteine in DL-form which is available at low cost by chemical synthesis is very advantageous to industrial practice because in the reaction system, L-homocysteine is converted to SAH by the action of SAHase while D-homocysteine is consecutively racemized to DL-homocysteine, and therefore all DL-homocysteine can be converted to SAH.

The reaction conditions may be properly selected. For example, the concentration of adenosine may be at least 1 mM, preferably 10 to 500 mM, and the concentration of D-homocysteine may be at least 1 mM, preferably 10 to 500 mM.

It should be understood that in the present invention, the term "homocysteine" also includes substances which yield homocysteine in the reaction system, such as homocystine and homocysteinethiolactone.

The pH of the reaction system may be 4 to 12, preferably 6 to 10. Adjustment of the pH may be carried out by an ordinary method, for example by using potassium phosphate buffer, Tris buffer, ammonium chloride buffer and glycine buffer.

The reaction temperature may be any temperature at which the reaction proceeds well and which does not affect the enzymatic activity, the substrates and the product. Usually, it is 15° to 60° C., preferably 20° to 50° C. The reaction time may be prescribed so that the conversion of the substrates to SAH increases. In the batchwise process, it is usually 0.1 to 48 hours, preferably 0.5 to 36 hours. As required, organic solvents such as acetone and ethanol and various surface-active agents may be added to the aqueous medium. A reagent for protecting the SH group, such as 2-mercaptoethanol or dithiothreitol, may be added in order to prevent homocysteine in the reaction system from changing to homocystine. The reaction may also be carried out in an atmosphere of nitrogen.

As a result, the reaction mixture containing SAH is obtained. SAH may be recovered from the reaction mixture by known methods. For example, SAH may be separated by a method comprising contacting the SAH-containing solution with a strong acid-type cation exchange resin to adsorb SAH, eluting the resin with sulfuric acid, and adding phosphotungstic acid to the eluate to precipitate SAH; or a method comprising contacting the SAH-containing solution with activated carbon to adsorb SAH, eluting the activated carbon with ethanol/water/concentrated aqueous ammonia (50:50:1), concentrating the eluate under reduced pressure, adjusting the pH of the concentrate to 7 with acetic acid, and then crystallizing SAH at 0° C.

The following Examples illustrate the present invention more specifically. It should be understood however that the invention is in no way limited to these examples.

In these examples, SAH was quantitatively determined by the following method.

Immediately after the end of the reaction, the reaction mixture was cooled to 0°–5° C., and perchloric acid was added to stop the reaction. The insoluble materials were removed by centrifugation. Potassium phosphate buffer (pH 7.0) was added to the supernatant liquid. The resulting potassium perchlorate was removed by centrifugation. A predetermined amount of the supernatant liquid was sampled, and the quantity of SAH in it was determined by high-performance liquid chromatography (Model 638-30 made by Hitachi Limited; column Cosmocil 5$C_{18}$; detector UV 260 nm).

EXAMPLE 1

One platinum loopful of *Pseudomonas putida* IFO 12996 or *Alcaligenes faecalis* IFO 12669 cultivated at 28° C. for 24 hours in an agar slant medium (pH 7.0) composed of 1 g/dl of glucose, 1.5 g/dl of peptone, 0.3 g/dl of yeast extract 0.3 g/dl of $K_2HPO_4$, 0.2 g/dl of NaCl, 0.02 g/dl of $MgSO_4.7H_2O$ and 2 g/dl of agar was inoculated in 500 ml of a heat-sterilized liquid medium adjusted to pH 7.0 and composed of 1 g/dl of glucose, 15 g/dl of peptone, 0.3 g/dl of yeast extract, 0.3 g/dl of $K_2HPO_4$, 0.2 g/dl of NaCl and 0.02 g/dl of $MgSO_4.7H_2O$ and cultivated with shaking at 28° C. for 40 hours. The cells were collected by centrifugal separation, washed with 0.1M potassium phosphate buffer (pH 8.0), and again centrifuged to obtain wet cells. Then, the wet cells of *Pseudomonas putida* IFO 12996 or *Alcaligenes faecalis* IFO 12669 in the amounts indicated in Table 1 were suspended in 1 ml of a substrate solution composed of 10 mM of adenosine, 10 mM of D-homocysteine and 100 mM of potassium phosphate buffer (pH 8.0), and the mixture was shaken at 30° C. for 2 hours to react the compounds. The results are shown in Table 1.

TABLE 1

| Run No. | Weight of the wet cells (mg) | | Amount of SAH yielded ($\mu$mole/ml) |
|---|---|---|---|
| | *Pseudomonas putida* IFO 12996 | *Alcaligenes faecalis* IFO 12669 | |
| 1-1 | 10 | 300 | 3.01 |
| 1-2 | 30 | 270 | 6.53 |
| 1-3 | 50 | 250 | 7.08 |

EXAMPLE 2

Fifty milligrams of wet cells of each of the microorganisms of the genus Pseudomonas shown in Table 2 obtained in the same way as in Example 1 and 250 mg of wet cells of *Alcaligenes faecalis* IFO 12669 were suspended in 1 ml of a substrate solution composed of 10 mM of adenosine, 10 mM of D-homocysteine and 100 mM of potassium phosphate buffer (pH 8.0), and the mixture was shaken at 30° C. for 2 hours to react the compounds. The results are shown in Table 2.

TABLE 2

| Run No. | Microorganism | Amount of SAH yielded ($\mu$mole/ml) |
|---|---|---|
| 2-1 | *Pseudomonas maltophilia* IFO 12020 | 0.93 |
| 2-2 | *Pseudomonas putida* IFO 3738 | 1.87 |
| 2-3 | *Pseudomonas aeruginosa* IFO 3445 | 2.40 |

EXAMPLE 3

One platinum loopful of *Saccharomyces cerevisiae* IFO 1805 cultivated at 28° C. for 48 hours in an agar slant medium (pH 6.0) composed of 5 g/dl of glucose, 0.5 g/dl of peptone, 0.1 g/dl of yeast extract, 0.2 g/dl of $KH_2PO_4$, 0.1 g/dl of $K_2HPO_4$, 0.02 g of $MgSO_4.7H_2O$ and 2 g/dl of agar was inoculated in 500 ml of a heat-sterilized liquid medium adjusted to pH 6.5 and composed of 5 g/dl of glucose, 0.5 g/dl of peptone, 0.1 g/dl of yeast extract, 0.2 g/dl of $KH_2PO_4y$, 0.1 g/dl of $K_2HPO_4$ and 0.02 g/dl of $MgSO_4.7H_2O$, and cultivated with shaking at 28° C. for 40 hours The cells were collected by centrifugal separation, washed with 0.1M potassium phosphate buffer (pH 8.0), and again centrifuged to obtain wet cells. Then, 300 mg of the wet cells and 50 mg of wet cells of *Pseudomonas putida* IFO 12996 obtained in the same way as in Example 1 were suspended in 1 ml of a substrate solution composed of 10 mM of adenosine, 10 mM of D-homocysteine and 100 mM of potassium phosphate buffer (pH 8.0), and the mixture was shaken at 37° C. for 4 hours to react the compounds. SAH was formed in an amount of 2.11 $\mu$moles/ml.

When the above reaction was carried out in the absence of the wet cells of Pseudomonas putida IFO 129906, no formation of SAH was observed.

EXAMPLE 4

The same reaction as in Example 3 was carried out except that Gibberella fujikuroi IFO 6605 was used and the resulting cells were collected by filtration. The amount of SAH yielded was 3.06 μmoles/ml. For comparison, the above procedure was repeated in the absence of the wet cells of Psudomonas putida IFO 12996. No formation of SAH was observed.

EXAMPLE 5

One platinum loopful of Micropolyspora angiospora IFO 13155 cultivated at 28° C. for 48 hours in an agar slant medium (pH 7.2) composed of 0.2 g/dl of yeast extract, 1 g/dl of soluble starch and 2 g/dl of agar was inoculated in 500 ml of a heat-sterilized liquid medium adjusted to pH 7.1 and composed of 1 g/dl of peptone, 0.5 g/dl of meat extract, 0.1 g/dl of yeast extract and 0.5 g/dl of NaCl, and cultivated with shaking at 28° C. for 48 hours to obtain wet cells. Using the wet cells the same reaction in Example 3 was carried out. The amount of SAH yielded was 1.78 μmoles/ml.

When the above procedure was repeated in the absence of the wet cells of Pseudomonas putida IFO 12996, no formation of SAH was observed.

EXAMPLE 6

One platinum loopful of Shizophyllum commune IFO 6504 cultivated at 28° C. for 96 hours in an agar slant medium (pH 5.0) composed of 2 g/dl of glucose, 0.3 g/dl of yeast extract, 0.3 g/dl of peptone, 0.1 g/dl of $KH_2PO_4$, 0.05 g/dl of $MgSO_4.7H_2O$ and 2 g/dl of agar was inoculated in 500 ml of a heat-sterilized liquid medium adjusted to pH 5.0 and composed of 2 g/dl of glucose, 0.3 g/dl of yeast extract, 0.3 g/dl of peptone, 0.1 g/dl of $KH_2PO_4$ and 0.05 g/dl of $MgSO_4.7H_2O$, and cultivated at 28° C. for 90 hours with shaking. The cells were collected by filtration. By using the resulting wet cells, the same reaction as in Example 3 was carried out. As a result, 0.49 μmole/ml of SAH was formed.

When the above reaction was carried out in the absence of the wet cells of Pseudomonas putida IFO 12996, no formation of SAH was observed.

EXAMPLE 7

The two kinds of wet cells obtained by the same method as in Example 1 were dried at room temperature for about 15 hours while passing air, and further dried in a vacuum desiccator containing phosphorus pentoxide at 5° C. for 1 day. Then, the dried cells were ground to a powder in a mortar, and again dried in the vacuum desiccator to prepare dried cells. Five milligrams of the dried cells of Pseudomonas putida IFO 12996 and 40 mg of the dried cells of Alcaligenes faecalis IFO 12669 were added to 1 ml of a substrate solution containing 10 mM of adenosine, 10 mM of D-homocysteine and 50 mM of potassium phosphate buffer (pH 8.0), and the mixture was shaken at 37° C. for 1 hour to react the compounds. The amount of SAH yielded was 5.90 μmoles/ml.

EXAMPLE 8

Ten milligrams of wet cells of Pseudomonas putida IFO 12996 prepared by the same method as in Example 1 and 500 U (the enzyme activity to form 1 picomole of SAH per hour at a pH of 7.0 and a temperature of 37° C. is defined as 1 U) of SAHase derived from a rabbit (a product of Sigma Co.) were added to 1 ml of a substrate solution composed of 1 mM of adenosine, 1 mM of D-homocysteine and 100 mM of potassium phosphate buffer (pH 8.0), and the mixture was shaken at 37° C. for 4 hours to react the compounds. The amount of SAH yielded was 0.031 μmole/ml.

When the above reaction was carried out in the absence of the wet cells of Pseudomonas putida IFO 12996, no formation of SAH was observed.

EXAMPLE 9

Wet cells (0.5 g) of Pseudomonas putida IFO 12996 prepared by the same method as in Example 1 and 3 g of wet cells of Alcaligenes faecalis IFO 12669 were added to 10 ml of a substrate solution composed of 50 mM of adenosine, 50 mM of D-homocysteine and 100 mM of potassium phosphate buffer (pH 8.0), and the mixture was reacted at 37° C. for 10 hours in a nitrogen atmosphere to react the compounds. SAH in an amount of 334 μmoles (128 mg) was synthesized in the reaction mixture.

Then, with ice cooling, 0.4 ml of a 30% aqueous solution of perchloric acid was added to stop the resolution action. Insoluble materials such as cell residues were removed by centrifugal separation. A 1M aqueous solution of $KHCO_3$ was added to the supernatant liquid to adjust its pH to 6.0, and the resulting precipitate of potassium perchlorate was removed by centrifugal separation. The resulting supernatant liquid was passed through a column ($H^+$-type column) of a strong acid-type cation exchange resin (Dowex 50x8). The column was washed with a 0.025 % aqueous solution of thiodiglycol and 2N sulfuric acid containing 0.025 % of thiodiglycol, and fractions eluted with 6N sulfuric acid containing 0.025 % of thiodiglycol were collected. A 20% aqueous solution of phosphotungstic acid was added to the fractions, and the resulting precipitate was collected by centrifugal separation, washed with cold water, and dissolved in 5 times its volume of acetone/water (50/50 v/v). The solution was extracted with isoamyl alcohol/ether (1/1, v/v). $BaCO_3$ was added to the resulting aqueous layer to adjust its pH to 3.9. The resulting $BaSO_4$ was removed by filtration, and the supernatant liquid was lyophilized to give 74 mg of a white solid. This white solid was determined to be SAH by silica gel thin-layer chromatography, high-performance liquid chromatography, paper chromatography, infrared spectroscopy and measurement of its specific rotation.

What is claimed is:

1. A process for producing S-adenosyl-L-homocysteine which comprises contacting adenosine with D-homocysteine in an aqueous medium in the presence of cells or treated cells of a microorganism of the genus Pseudomonas having the ability to racemize D-homocysteine to DL-homocysteine and in the present of S-adenosyl-L-homocysteine hydrolase, thereby synthesizing S-adenosyl-L-homocysteine and thereafter collecting it.

2. The process of claim 1 wherein the microorganism cells are used as cells in the culture broth, resting cells or dry cells.

3. The process of claim 1 wherein the treated microorganism cells are used and are crushed cells or a cell-free extract.

4. The process of claim 1 wherein the S-adenosyl-L-homocysteine hydrolase is used in the form of cells or treated cells of a microorganism containing S-adenosyl-L-homocysteine hydrolase.

5. The process of claim 4 wherein the microorganism containing S-adenosyl-L-homocysteine hydrolase is used in the form of cells in the culture broth, resting cells or dry cells.

6. The process of claim 4 wherein the treated cells of the microorganism containing S-adenosyl-L-homocysteine hydrolase are used in the form of crushed cells or a cell-free extract.

7. The process of claim 4 wherein the microorganism containing S-adenosyl-L-homocysteine hydrolase is a microorganism of the genus Alcaligenes, Saccharomyces, Gibberella, Micropolyspora or Shizophyllum.

8. The process of claim 1 wherein adenosine is contacted with D-homocysteine at a temperature of 15° to 60° C. for 0.1 to 48 hours.

9. The process of claim 1 wherein the microorganism of the genus Pseudomonas is selected from the group consisting of *Pseudomonas putida*, *Pseudomonas aeruginosa* and *Pseudomonas maltophilia*.

10. The process of claim 1 wherein the D-homocysteine is used in the DL-form whereby L-homocysteine is converted to S-adenosyl-L-homocysteine and the D-homocysteine is racemized to DL-homocysteine.

11. The process of claim 1 which comprises contacting at least one mM of adenosine with at least one mM of D-homocysteine.

12. The process of claim 11 wherein the concentration of adenosine is from 10 to 500 mM and the concentration of D-homocysteine is from 10 to 500 mM.

13. The process of claim 8 wherein adenosine is contacted with D-homocysteine at a pH in the range of 4 to 12.

14. The process of claim 1 wherein adenosine is contacted with D-homocysteine at a pH of 6 to 10 and a temperature of 20° to 50° C. for a period of from 0.5 to 36 hours.

15. The process of claim 14 wherein the concentration of adenosine is from about 10 to 500 mM and the concentration of D-homocysteine is from about 10 to 500 mM.

* * * * *